United States Patent
Pugliese et al.

(12)

(10) Patent No.: US 6,309,656 B1
(45) Date of Patent: Oct. 30, 2001

(54) COSMETIC AND SKIN PROTECTIVE COMPOSITIONS

(76) Inventors: Peter T. Pugliese; Steven M. Pugliese, both of Pugliese & Associates, 4408-B Reading Pike, Reading, PA (US) 19605

( * ) Notice: Subject to any disclaimer, the term of this patent is extended or adjusted under 35 U.S.C. 154(b) by 0 days.

(21) Appl. No.: 09/386,235

(22) Filed: Aug. 31, 1999

Related U.S. Application Data

(60) Provisional application No. 60/110,155, filed on Nov. 27, 1998.

(51) Int. Cl.⁷ .............................. A61K 7/13; A61K 7/075; A61K 31/195
(52) U.S. Cl. ...................... 424/401; 424/70.12; 514/566
(58) Field of Search ................................ 424/70.12, 401; 514/566

(56) References Cited

U.S. PATENT DOCUMENTS

| 4,129,644 | 12/1978 | Kalopissis et al. | ...................... 424/59 |
| 4,786,493 | 11/1988 | Smith et al. | ............................. 424/59 |
| 4,814,351 | * 3/1989 | Mathews et al. | ..................... 514/566 |
| 5,145,644 | 9/1992 | Park et al. | .............................. 422/28 |
| 5,482,703 | * 1/1996 | Pings | .................. 454/70.12 |

FOREIGN PATENT DOCUMENTS

| 264760 | 10/1949 | (CH) . |
| 268157/A1 | 5/1989 | (DE) . |
| WO 9955301 A | * 4/1998 | (FR) . |
| 744438 | 2/1956 | (GB) . |
| 1995-368055 | 9/1996 | (JP) . |
| 1998-69412 | 8/1998 | (JP) . |

OTHER PUBLICATIONS

Derwent 1998–320407 Nov. 20, 1997 abstract of Russian Patent R112093032.
Nature Mgazine Aug. 26, 1994/P.268 unites States, Organic Accelerators, etc.

* cited by examiner

*Primary Examiner*—Jean F. Vollano
*Assistant Examiner*—Mina Haghighatian
(74) *Attorney, Agent, or Firm*—A. R. Eglington

(57) ABSTRACT

A hair and scalp formulation based on a peroxidase enzyme and synergistic yeast extract therefore. It entails a chemically-inert carrier material, a germicidal/preservative agent, and a metal chelating agent. A skin protective formulation based on peroxidase enzyme and yeast extract. It entails a polymer carrier, a fatty acid emollient, a co-emulsifier of an amino acid complex essential to a fatty acid; an emulsifying agent; a skin healing agent, and a germicidal surfactant. An aqueous formulation adapted for topical hair rinsing consisting of a peroxidase enzyme, a yeast extract adapted to enhance the activity of the enzyme and a cationic hair conditioning agent selected from water-soluble thickening resins.

8 Claims, No Drawings

COSMETIC AND SKIN PROTECTIVE COMPOSITIONS

This application claims priority to provisional application No. 60/110,155, filed Nov. 27, 1998.

CROSS-REFERENCE TO OTHER FILINGS

This is a regular patent application submitted for an official filing receipt under 35 U.S. Code Section 111(a). It relates to U.S. Disclosure Document No. 316,635 filed Sep. 4, 1992 and titled: Catalase Protective Hand Cream Against Peroxide Compounds.

FIELD OF THE INVENTION

A cosmetic and skin protective composition containing a peroxide-destroying compound, an enzyme protection and augmenting compound, and a metal chelating compound. This composition being useful to protect the skin and hair from oxidative damage and topical irritation and methods for making and using such protective compositions. A method to improve the coloring process for hair involving inclusion of a peroxide destroying compound in the dyeing process itself.

BACKGROUND OF THE INVENTION

In the hair treatment art, often involving use of hydrogen peroxide as a commonly used reagent, in the fine art of bleaching, and in dyeing and curling human hair (so-called permanent waving), the concurrent deleterious effects of this important, but needed, reagent have long been recognized as entailing chemical irritation of human skin.

In the known methods of coloring hair, the peroxide serves to develop color in oxidative dyes, in situ, and to neutralize sulfhydryl anions in the reduction of keratinic materials, like human hair. In both reactions, the reaction of peroxide is not readily controlled, as it can act to both increase or decrease the intensity of the staining reaction, should excess peroxide remain in the hair. The usual practice, with somewhat uneven results, is to rinse the hair in an effort to remove the residual peroxide. Catalase is a naturally occurring enzyme in biological systems, being a peroxidase enzyme that converts a peroxide to water and oxygen.

The same peroxide and catalase enzyme are used in waving of hair. After the peroxide neutralizes the reducing agent, as noted, a water rinse is used to remove the residual peroxide. However, any residual peroxide remaining acts as both an oxidizing agent and a reducing agent. As a reducing agent, it can break keratinic disulfide bonds and damage the waving process. As an oxidizing agent, it produces reactive oxygen radicals, such as hydroxyls, which can destroy hair fibers.

It is known that the skin-adverse effects can be ameliorated by employing an enzyme that could arrest the oxidase reaction, before it contacts the hands, of the beautician, and/or the scalp skin of the client. G. Kalopissis et al, U.S. Pat. No. 4,129,644 (1978) taught protecting the skin with cosmetic compositions containing a super oxide dismutase (SOD) enzyme. Certain SOD enzymes are extracted from marine bacterial strains. Disclosed were foam dye compositions and hair dyes in cream formulations. No other adjuvants for such active ingredient were taught. The benefit was in applying to the hair, an SOD enzyme in an effective amount, to maintain the keratinic structure of the hair, but not of the scalp-skin. Park et al, U.S. Pat. No. 5,145,644 (1992) also relates to peroxide destroying compositions, such as catalase, but involves using a barrier coating to delay release of the catalase, for a time period after the formulation is contacted with the peroxide containing aqueous medium.

The enzyme formulations are in core tableted forms and the coating is of a water-soluble, barrier material, which is conveniently a polymeric material like cellulose derivative. The disclosed utility is for the disinfection of contact lenses. There is no useful material suggested by Park, et al, to enhance the peroxide-reducing power of the catalase enzyme; nor would such solid, unit dosage forms of such an enzyme have any application in the hair treating and scalp protection process.

It is known that catalase can be deactivated by certain toxic heavy metals and organic compounds known to interfere with biological electron transport.

In the prior art, use of an alcoholic extract of Baker's yeast (Sacharomyces Cerevisiae) is reported to stimulate respiration of skin, in liver and in live yeast cells. Later Kreke et al reported (1945) that activity of horseradish-derived peroxidase could be increased by addition of such a yeast extract. One interesting incidental finding was the protective effect that the yeast extract had on the action of known enzyme inhibitors in the respiratory chain, such as azides, and cyanides. The action of such inhibitors may also have some effect on the addition of catalase and other peroxidase inhibitors.

It is a principal object of the present invention to provide a skin protective ointment, or hand cream, containing catalase enzyme now in a form useful against the peroxide compound side effects on human skin.

It is a still further object to provide a skin protective ointment which enhances the peroxide-reducing activity of catalase in the presence of toxic metals and organics that inhibit electron transport.

It is a further object of the invention to provide a catalase containing ointment that will protect the skin with a water resistant barrier, while decomposing the excess (residual) active peroxide not already used up in the hair bleaching process.

Yet another object of the invention is to provide a method for more uniformly dyeing hair in a limited time by admixing of an augmented natural catalase compound activity into an oxidative hair dye, for hair dyeing with the peroxide ingredient.

A still further object of this invention is to provide a composition that may be sprayed or rinsed in the hair which will neutralize and destroy residual peroxides, following the coloring or other chemical treatments of hair that employ hydrogen peroxides, or other peroxides, in the hair treatment process.

SUMMARY OF THE INVENTION

New compositions, methods for making of such protective compositions, and methods for selectively destroying residual hydrogen peroxide in the hair dyeing and hair waving arts, have been discovered. A selected polymer (typically a polysaccharide) acts as carrier for the catalase enzyme and adjuvant, but still allows it to react with the peroxide in the dyeing composition. We have found that addition of a selected yeast extract increases catalase activity on a milligram for milligram basis. It is possible to gain the same amount of free oxygen generation from peroxide degradation via catalase, while decreasing the catalase concentration, by adding a small amount of the selected yeast extract. The present invention also teaches a method of destroying residual peroxide on the skin-scalp, before it has time to react with the skin/scalp tissues. We also add skin respiratory factor (SRF) to catalase in aqueous solution, in the presence of $H_2O_2$ toxic metals, to determine if there was a beneficial effect, as measured by increased $O_2$ production.

The active ingredient catalase may be derived from both plant and animal sources, or from bacterial cultures, as in the mentioned Kalopissis '644 U.S. patent. It may also be genetically engineered from bacterial sources. The scalp protective material may include polyvinylpyrrolidone, guar gums and other natural gums, hydroxycellulose derivatives and acrylate derivative. This provides a layer of protection on the scalp that will impede the hydrogen peroxide from reaching the scalp and for neutralizing any peroxide that may break through the barrier.

This protective material is preferably a cross-linked polysaccharide, serving as a barrier to skin harmful ingredients, like peroxides. The multipolymer composition spontaneously forms multiple layers. A third layer is formulated of silicone carrier, with a saturated fatty alcohol, like behenol alcohol, and the catalase which are laid down as the outermost layer. This multi-layer formulation is desirably water resistant, but not water proof. This advantageous feature allows the skin treating residual peroxide to penetrate same to a depth that the outer layered catalase can readily interact with the excess peroxide.

In one embodiment, a hand cream will protect the operator with a water-resistant barrier, predicated on the use of silicone-based materials and acrylate containing the catalase. This hand-treating formulation comprises a silicone emollient, water resistant base, either water-in-oil, or oil-in-water type of emulsion. It contains the enzyme in 500 units per gram of formulation up to 10,000 or more units per gram.

In another embodiment, a peroxide destroying compound, an aqueous rinse will protect the hair from further oxidation/reduction, when the hair is treated with a reducing agent like a thioglycolate; and then is neutralized with peroxide. It is noted that the addition of a Baker's yeast extract will augment the peroxidase activity, and it may further preclude toxic substances, like azide ions, from inhibiting the oxidation effect of the catalase.

The inventive composition is a cosmetic product useful to protect the skin against the irritant effects of hydrogen peroxide, residual or either on the hands of the operator, or on the forehead and/or scalp of the client. In the described rinse formulation, the product can serve to neutralize and/or destroy the oxidative nature of peroxides residual on the hair remaining after coloring or after permanent waving.

A significant incidental findings was the protective effect of the yeast extract on counteracting adverse action of potential environmental toxins, such as azides, or cyanides, which are known to inhibit enzymes of the respiratory chain. The yeast extract not only helps to protect the enzyme, but also augments the enzyme action of catalase by increasing the rate of the reaction without increasing the amount of catalase. A second observation was the effect on transition metals, such as iron and copper. The addition of an iron chelator such as sodium phytate, protects the catalase, while at the same time helps to prevent the conversion of peroxide to hydroxyl radical (ion) via the Fenton reaction.

DETAILED DESCRIPTION OF THE INVENTION

Peroxidase enzymes decompose peroxides to water and free oxygen. Available enzymes include catalase and horse-radish peroxidase, while examples of treatable peroxides are hydrogen peroxide and lipid-bound peroxides.

The synergetic yeast extracts are the biologically active components of yeast cells, and are provided to inhibit the deleterious activities of toxic organic compounds, like pesticides and herbicides that would impede peroxidase activity.

A number of polymers can act as carriers for the catalase, these include polyvinylpyrrolidone-based polymers, guar gums, and other natural gums, water soluble, hydrocelluose derivatives and methacrylate based polymer derivatives.

Emulsifiers serve to dispersed aqueous mixtures in oils (or lipids in aqueous media) and make for a stable formulation. For example, glycerol monostearate is the primary emulsifier in the presently disclosed formulations, while PEG 2000 DPS (a polyethylene glycol) condensation polymer is a co-emulsifier.

Among suitable emollients and scalp moisturizers are Permethyl 101A, an alkane stearic acid, octyl palmitate; organosiloxane polymers, like Silicone 200; silicone oils, like Dimethicone DC 556; and ethoxylated derivatives of lanolin and lanolin components (Solulan PB 20). Silicone oils also serve as waterproofing agents, such as Silicone 200 and Dimethicone DC 556.

Allantoin (5-ureido hydantoin) is a natural urea derivative having anti-inflammatory properties and a healing action. Panthenol is the water-soluble alcohol corresponding to pantothenic acid, the latter a member of the Vitamin B complex, also with healing properties.

Demacryl 79 is an acrylic acid derivative that acts as a skin barrier to protect skin by forming a film; Carbomer 940, a hydroxycellulose, is a thickening (jelling) agent, which is neutralizable with triethanolamine (TEA); and the amino lipid complex, (for example, HEPES linoleate) is a co-emulsifier and novel anti-inflammatory agent. The oat protein is obtainable from natural oat grains, which contain biological antioxidants and healing agents.

Preparation of a Catalase

EXAMPLE I

Many biological sources of catalase are available from both plants and animals and bacterial cultures (Compare Kallopissis U.S. Pat. No. 4,129,644). For the present, a fungal source, aspergillus niger, appears the most active and economic source. A commercially available source of catalase enzyme, with standardized peroxidase activity, is the trademarked product, FERMCOLASE, available from Genencor International, Cambridge Place, Rochester, NY, and identified by product code 1000. FERMCOLASE 1000 maintains maximum activity when stored at 2—4° C. It's activity is expressed in Baker Units (BU). One BU is defined as the amount of enzyme which will decompose 264 mg $H_2O_2$ in one hour, at 25° C., pH 7.0. FERMCOLASE-1000 enzyme is active in the temperature range of 0—65° C.

Preparation of Yeast Extract Used as Enzyme Augmenting Agent-Skin Respiratory Factor (SRF)

EXAMPLE II

While yeast extract, per se, has only slight peroxidase activity and no catalase activity, yeast extracts are known to accelerate the activity of both peroxidase and catalase. Live Baker's Yeast is obtained in moist cake form from several sources. The live yeast cakes are introduced into a reflux vessel with the alcohol. Refluxing is carried out after which the hot slurry is filtered to provide a clear straw yellow solution. Alcohol concentration at this point and at the time of filtration is intermediate, the dilution being due to the water present in the yeast cakes. The extraction therefore recovers those materials in yeast which are soluble in the diluted alcohol at this state.

The clear filtrate is concentrated under vacuum to remove the alcohol and most of the water. A final filtration step yields a clear brown, viscous aqueous solution with soluble non-volatile content of 45 to 55 percent. This yeast extract is available commercially from GIST BROCADESE, King of Prussia, Pennsylvania, as live yeast cell derivative. It is termed for these purposes as SRF.

EXAMPLE III

Protective Skin Cream

Catalase enzyme (source FERMCOLASE 1000) is formulated into an oil-in-water-based emulsion. A useful formulation consists of lipids, silicones, derivatives, emulsifiers, preservatives, and the catalase. A representative composition, omitting the yeast extract of Example II, is as tabulated below:

|  | By Weight |
|---|---|
| Silicones | 20 |
| Behenyl Alcohol, diluent | 10 |
| Emulsifier | 5 |
| Protective Polymer | 1 |
| Preservative | 1.0 |
| FERMCOLASE 1000 | 3.0 |
| Water | QS |

All ingredients are percentages by weight, such as in grams.

The protective polymer may be synthetic, such as modified acrylic acid derivative, a modified polyvinyl pyrrolidine derivative or natural gums like guar gum, or other natural polysaccharides. The emulsifier may be anionic, non-ionic or cationic, or it may be some other form of dispersion stabilization. This formulation is tested as a cream.

EXAMPLE IV

A cream containing 4000 units of catalase per milliliter was prepared and a 0.1 milliliter aliquot was spread over a glass slide and allowed to dry by air exposure. The slide was immersed in a 12% solution of hydrogen peroxide and immediately observed to produce copious quantities of CAS (oxygen) bubbles. This experiment was repeated after one hour, 24 hours, and at 96 hours with no observable change in oxygen production. This confirmed its peroxidase activity in the cream formulation.

EXAMPLE V

Supportive Clinical Data

A preparation containing 4000 units of catalase per milliliter of cream of Example III was applied to the right hand of each of five subjects, and the hands were then exposed to 12% peroxide for 1 to 2 minutes. The left hands were not pre-treated with cream, and were exposed to in the same peroxide concentration for 1 to 2 minutes. Ten minutes after exposure, the left hands showed oxidation effects, manifested by white discoloration of the skin, while the right hands showed no visual change.

EXAMPLE VI

An Aqueous Composition Adapted to Hair Rinsing

This composition is employed to remove residual peroxide after the hair coloring and/or waving operation is completed.

| Catalase enzyme (Fermcolase-1000) | 1.3% by weight |
|---|---|
| Yeast Extract (Example II) | 0.01% by weight |
| Cationic Conditioning Agent* | 0.5–1% by weight |
| Water QS | 100% |

All ingredients are percentages by weight.

*MONOQUAT PTC, Mona Industries, Patterson, N.J. is cocamidopropyl phosphatidyl-polyethylene glycol dimonium chloride.

*HEPES ester which is 4-(2-hydroxyethyl)-1-piperazine-ethane sulfonic acid, linoleate ester, the synthesis and utility of which is first disclosed in my copening (with another) U.S. patent application Ser. No. 09/200,482, filed Nov. 27, 1998, titled ZWITTERIONIC-FATTY ACID COMPOUNDS, and now U.S. Pat. No. 6,114,337.

EXAMPLE VII

An alternate Aqueous gel Composition Adapted to Hair Protection

|  | Wt % |
|---|---|
| Catalase enzyme | 2.0 |
| Yeast Extract | 0.05 |
| Carbopol 940 (water-soluble, thickening resin) | 0.5 (Source: B. F. Goodrich) |
| Triethanol amine 99% | 0.2 (commodity chemical) |
| A preservative agent | 0.1 to 1.0 |
| Water QS | 100.0 |

In hair care salons, the above formulation (Example VII) has been used on the scalp and forehead of those undergoing both coloring procedures and permanent waving with excellent results. The product has markedly reduced the irritation to the hands of the cosmeticians, normally seen with $H_2O_2$ use and/or the use of other oxidative agents employed in hair dressing.

EXAMPLE VIII

An Alternative Protective Skin Cream

This cream is characterized by inclusion of a waterproof polymer barrier, polymer healing agents, and an antioxidant agent which destroys peroxides residual on the skin.

| | Useful Range |
|---|---|
| Deionized water | Q.S. |
| Permethyl 101A (an alkane) emollient | 8–10% by weight |
| Carbomer 940 (jelling agent) | 0.20% by weight |
| Stearic Acid (moisturizer) | 2–4% by weight |
| Glycerol Stearate (Co-emulsifier) | 1–3% by weight |
| Octylpalmitate (moisturizer) | 1–2% by weight |
| Dermacryl-79 (film forming barrier) | 0.5–2% by weight |
| Catalase enzyme (antioxidant) | 0.5–3% by weight |
| HEPES Linoleate (anti-inflammatory agent)* | 1–2% by weight |
| Panthenol (healing agent) | 1.5–2% by weight |
| Triethanol Amine (neutralizing agent) | 1.3% by weight |
| Polyethylene Glycol 2000 | 1–2% by weight |
| Dimethicone 556 (emollient) | 0.5–1% by weight |
| Silicone 200 (emollient) | 0.5–1% by weight |
| Oat Protein (antioxidant) | 1–2% by weight |
| Germaben II diazourea compound (preservative) | 1% by weight |
| Phytic Acid | 0.5% by weight |
| Allantoin (healing agent) | 0.5–1% by weight |

The above cream formulation is prepared as follows:
1. Dissolve allantoin and panthenol in water. Add TEA and begin heating to 70° C.
2. Add the Dermacryl slowly and disperse it thoroughly.
3. At 50° C., sift in Carbomer 950, then mix well.
4. Combine the oil phase ingredients and heat to 70° C. Use Homomix (homogenize) to incorporate the oat protein and HEPES linoleate.
5. Add the oil phase to the water phase at 70° C., using propeller agitation. Mix well.
6. Cool to 50° C., add Germaben preservative and fragrance. Lower pH with 50% citric acid to desired thickness.

What is claimed is:

1. A hair and scalp protective formulation containing a peroxidase enzyme with standardized peroxidase activity and a synergistic compound which enhances the peroxide-reducing activity of the enzyme by inhibiting the deleterious effects of any organic compounds, or heavy metals that would normally inhibit the enzyme, consisting essentially of a water dispersible formulation, consisting essentially of:
    (a) a yeast extract adapted to enhance the peroxidase activity of the peroxidase, such yeast extract being known as live yeast cell extract;
    (b) a chemically-inert carrier material for the enzyme selected from the group consisting of polyvinylpyrrolidone, aqueous medium-dispersible cross-linked polysaccharides, guar gums, xanthine gums, alginic acid, chitin, acrylate, imidozolidnyl ureas, phenoxyethanols, and chloroxylenols;
    (c) a germicide/preservative agent selected from the group consisting of 2-bromo-2-nitropropane-1,3-diol, quanternium-15, benzoisothiazide, and parabens esters; and,
    (d) a metal chelating agent selected from the group consisting of phytic acid, sodium phytate, and a hydroxylated benzoic acid.

2. The formulation of claim 1 wherein the enzyme is catalase and the polysaccharide are hydroxycellulose compounds.

3. A skin protective formulation in the form of an oil-in-water emulsion consisting essentially of:
    (a) a peroxidase enzyme with standardized activity selected from the group consisting of catalase enzyme and/or horseradish peroxidase;
    (b) a polymeric carrier for the peroxidase adapted to permit the peroxidase enzyme to react with any peroxide residual from a hair dyeing process, with the carrier being selected from a group consisting of acrylate derivatives; and polysaccharide derivatives;
    (c) a saturated fatty acid alcohol, serving as an emollient moisturizer and as a protective barrier;
    (d) an aminolipid complex serving as a co-emulsifier and consisting essentially of at least one amino acid compound esterified to a fatty acid;
    (e) an emulsifying agent selected from the group of non-ionic, anionic, or cationic surfactants;
    (f) a skin healing agent selected from the group consisting of allantoin and panthenol; and,
    (g) a germicidal surfactant selected from the group consisting of 2-bromo-2-nitropropane-1,3-diol, quaternium-15, benzoisothiazide, and parabens esters; and,
    (h) water of substantially neutral pH in quantum sufficient to make up the stated ranges for the active components (a) to (g).

4. The formulation of claim 3 wherein the carrier is selected from the group consisting of dimethicone, and dimethicone polyols.

5. The formulation of claim 3 wherein the carrier is hydroxymethyl cellulose.

6. The skin protective formulation of claim 3 wherein the enzyme is catalase and the esterified amino acid compound is HEPES linoleic acid.

7. An aqueous gel composition for hair protection during hair processing comprising:
    (a) a peroxidase enzyme with standardized peroxidase activity selected from the group consisting of catalase enzyme and horseradish peroxidase;
    (b) a yeast extract to enhance the peroxidase activity of the peroxidase, such yeast extract being known as live yeast cell extract;
    (c) a gelling agent;
    (d) a neutralizing agent for the gelling agent;
    (e) a preservative agent, and,
    (f) water QS.

8. A protective formulation of claim 1 wherein the peroxidase enzyme is selected from the group consisting of catalase enzyme and horseradish enzyme.

* * * * *